United States Patent [19]

Van Endschot et al.

[11] Patent Number: 5,073,917
[45] Date of Patent: Dec. 17, 1991

[54] X-RAY EXAMINATION APPARATUS

[75] Inventors: Johannes G. Van Endschot; Cornelis M. Van Doorn, both of Eindhoven, Netherlands

[73] Assignee: U.S. Philips Corporation, New York, N.Y.

[21] Appl. No.: 614,414

[22] Filed: Nov. 15, 1990

[30] Foreign Application Priority Data

Nov. 22, 1989 [NL] Netherlands ............. 8902885

[51] Int. Cl.$^5$ ............................................. H05G 1/02
[52] U.S. Cl. .................................... 378/197; 378/196; 378/198; 378/193
[58] Field of Search ............. 378/197, 196, 193, 189, 378/15, 21, 198

[56] References Cited

U.S. PATENT DOCUMENTS

| | | | |
|---|---|---|---|
| 2,595,260 | 5/1952 | Hollstein | 378/197 |
| 3,281,598 | 11/1963 | Hollstein | 188/158 |
| 4,150,297 | 4/1979 | Borggren | 378/197 |
| 4,741,007 | 4/1988 | Virta et al. | 378/89 |
| 4,961,214 | 10/1990 | Van Endschot et al. | 378/197 |
| 4,989,229 | 1/1991 | Negrell et al. | 378/197 |
| 5,014,293 | 5/1991 | Boyd et al. | 378/197 |

FOREIGN PATENT DOCUMENTS 1175032 12/1969 United Kingdom .

Primary Examiner—Janice A. Howell
Assistant Examiner—Don Wong
Attorney, Agent, or Firm—William Squire

[57] ABSTRACT

In an X-ray examination apparatus, comprising a column, a mount which is connected to the column and which is rotatable about an axis, and a C-shaped carrier which is journalled in the mount, there is provided a friction roller which serves to drive and brake the C-shaped carrier and which bears against a contact face provided along the carrier. The carrier is thus locked in a play-free manner and can be readily adjusted by hand. Because the friction roller is journalled in a carriage which is displaceable with respect to the mount, a pressure exerted on the contact face by the friction roller is adjustable.

24 Claims, 4 Drawing Sheets

X-RAY EXAMINATION APPARATUS

BACKGROUND OF THE INVENTION

FIELD OF THE INVENTION

The invention relates to an X-ray examination apparatus, comprising a column, a mount which is rotatable about an axis and which is connected to the column, a C-shaped carrier which is journalled in the mount and which carries an X-ray source and an X-ray detector which are connected to its ends so as to face one another, which carrier is displaceable in the mount along a segment of circle, and also comprising displacement means which bear against the carrier on a contact face and which comprise a drive shaft which is connected to the mount, it being possible to lock the carrier with respect to the mount by blocking the displacement means.

DESCRIPTION OF THE PRIOR ART

An X-ray examination apparatus of this kind is known from British Patent Specification GB 1,175,032. The cited Patent Specification describes an X-ray examination apparatus which is suitable for irradiating an object from a plurality of directions in order to form an X-ray image. When the mount is rotated about the axis and the carrier is translated in the mount, an imaginary ray between the X-ray source and the X-ray detector rotates about a point which is formed by the intersection of the axis and the ray (the isocenter). In order to prevent irrelevant structures from overlapping medically interesting details of an object to be imaged which is situated in the isocenter a number of different projections of the object to be imaged is required. The position of an object to be imaged which is situated in the isocenter does not shift in the X-ray image during the various projections. Displacement of the C-shaped carrier with respect to the mount is realized by way of an electric motor which drives the drive means which include a gearwheel. The gear wheel meshes with exterior teeth of the C-shaped carrier. In the case of a power failure during the examination or when a fast adjustment of the position of the X-ray source and the X-ray detector with respect to the object to be examined is necessary, it is advantageous when the C-shaped arm can be displaced by hand. For a reproducible and vibration-free adjustment of the X-ray source and the X-ray detector it is desirable that the carrier can be locked by the displacement means without play with respect to the mount.

It is to be noted that U.S. Pat. No. 3,281,598 describes an X-ray examination apparatus in which a C-shaped carrier can be displaced in a mount and is journaled therein by means of ball bearings. These ball bearings, however, serve to reduce the friction upon displacement of the C-shaped carrier in the mount and do not serve to drive and lock the carrier in the mount. For driving the carrier the X-ray examination apparatus described in the cited Patent Specification comprises drive means in the form of a gearwheel and a cooperating chain which is guided about the carrier.

SUMMARY OF THE INVENTION

It is an object of the invention to provide an X-ray examination apparatus which satisfies the described requirements as much as possible. To achieve this, an X-ray examination apparatus in accordance with the invention is characterized in that the displacement means comprises a friction roller.

The use of a friction roller enables accurate displacement and locking of the C-shaped carrier in the mount, because the rigidity of the friction roller contacting the contact face is high. The contact face may be flat when use is made of the friction roller, and need not be provided with exterior teeth or a chain for force transmission between the displacement means and the C-shaped carrier. The construction of the C-shaped carrier is thus simplified.

A preferred embodiment of an X-ray examination apparatus in accordance with the invention is characterized in that the drive shaft is journalled in a carriage which is displaceable with respect to the mount in a direction extending transversely of the contact face, a pressure member interconnecting the carriage and the mount and pressing the friction roller against the contact face.

The friction roller can be pressed against the contact face with a higher or a lower force by displacement of the carriage with respect to the mount, so that a force exerted on the contact face by the friction roller can be adapted to the balancing of the X-ray examination apparatus. If the mass center of the X-ray source and the X-ray detector coincides with the isocenter, the force to be exerted on the contact face by the friction roller for displacement or locking of the C-shaped carrier in the mount is comparatively low. However, if the mass center of the X-ray source and the X-ray detector is not situated in the isocenter, which may be the case when the distance between the X-ray detector and the X-ray source is changed in order to adjust an enlargement of the X-ray image to be formed, the X-ray examination apparatus is usually in a state of unbalance. In that case the force to be exerted by the friction roller in order to displace or lock the C-shaped carrier is higher.

A further preferred embodiment of an X-ray examination apparatus in accordance with the invention is characterized in that the pressure member comprises a spring.

When a spring is used as the pressure member, the force exerted on the contact face by the friction roller is constant. The force to be delivered by the pressure member is preferably adjustable.

A further preferred embodiment of an X-ray examination apparatus in accordance with the invention is characterized in that the pressure member is adjustable.

Because the motor is connected to the carriage, the transmission of rotation from the motor to the friction roller is simple. Shocks or vibrations which are transmitted to the friction roller via the C-shaped carrier displace the carriage in its entirety, without relative displacement occurring between the motor and the friction roller. The driving of the friction roller by the motor is, therefore, very constant.

Another preferred embodiment of an X-ray examination apparatus is characterized in that the motor is connected to the carriage and is displaceable together with the carriage with respect to the mount.

Manual adjustment of the X-ray examination apparatus is facilitated when the motor is uncoupled.

Another preferred embodiment of an X-ray examination apparatus in accordance with the invention is characterized in that the motor can be coupled to the drive shaft via a drive coupling.

The C-shaped carrier can be locked with respect to the mount by means of the brake clutch. Should the motor be deactivated due to a power failure, the position of the carrier can be locked by activation of the brake clutch, for example via an emergency power supply source. The carrier can also be locked by means of the brake clutch in the case of manual operation where the motor is uncoupled from the drive shaft or is completely absent.

BRIEF DESCRIPTION OF THE DRAWING

Some embodiments of an X-ray examination apparatus in accordance with the invention will be described in detail hereinafter with reference to the accompanying drawing. Therein.

DESCRIPTION OF THE PREFERRED EMBODIMENTS

Figure 1:
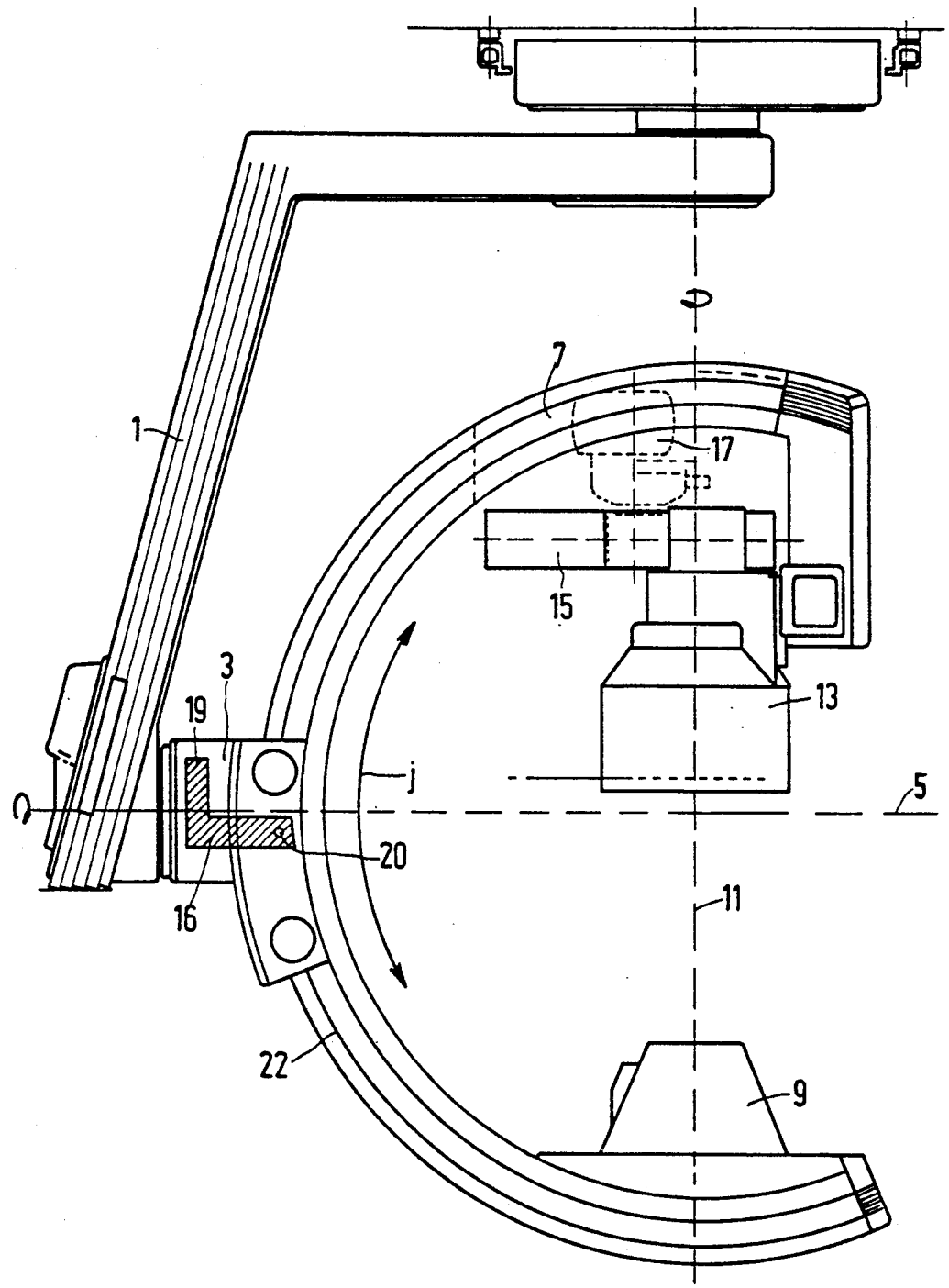
FIG. 1 is a side elevation of an X-ray examination apparatus in accordance with the invention.

FIG. 1 shows a mount 3 which is suspended from a column 1 and which is rotatable about an axis 5. In the present embodiment, the column 1 is suspended from a ceiling, but it may also rest on the floor in another embodiment. In the mount 3 there is journalled a C-shaped carrier 7 which is displaceable in the mount 3 along a segment of circle in the direction of arrow J. To a first end of the C-shaped carrier 7 there is secured an X-ray source 9 for emitting an X-ray beam along an imaginary ray 11. Opposite the X-ray source 9 there is arranged an X-ray detector 13, for example an X-ray image intensifier tube, whereto, for example, a television pick-up tube 15 and a cine camera 17 are coupled. An object which is situated at the point of intersection of the ray 11 and the axis 5 (the isocenter) is irradiated by the X-ray beam. An X-ray projection image is detected on the entrance of the X-ray detector 13 and applied to the cine camera 17 or the television pick-up tube 15 as an intensified optical image. After manual displacement of the carrier 7 in one of directions j, the carrier 7 is locked with respect to the mount 3 by way of a friction roller 20 which bears against a contact face 22, situated along the circumference of the carrier 7, and which is connected to a brake via a drive shaft which is not shown in the Figure. When the carrier 7 is driven in the mount 3 by means of a motor 19, the friction roller 20 is rotated by the motor 19 via the drive shaft, so that the carrier 7 is displaced with respect to the mount 3.

Figure 2:
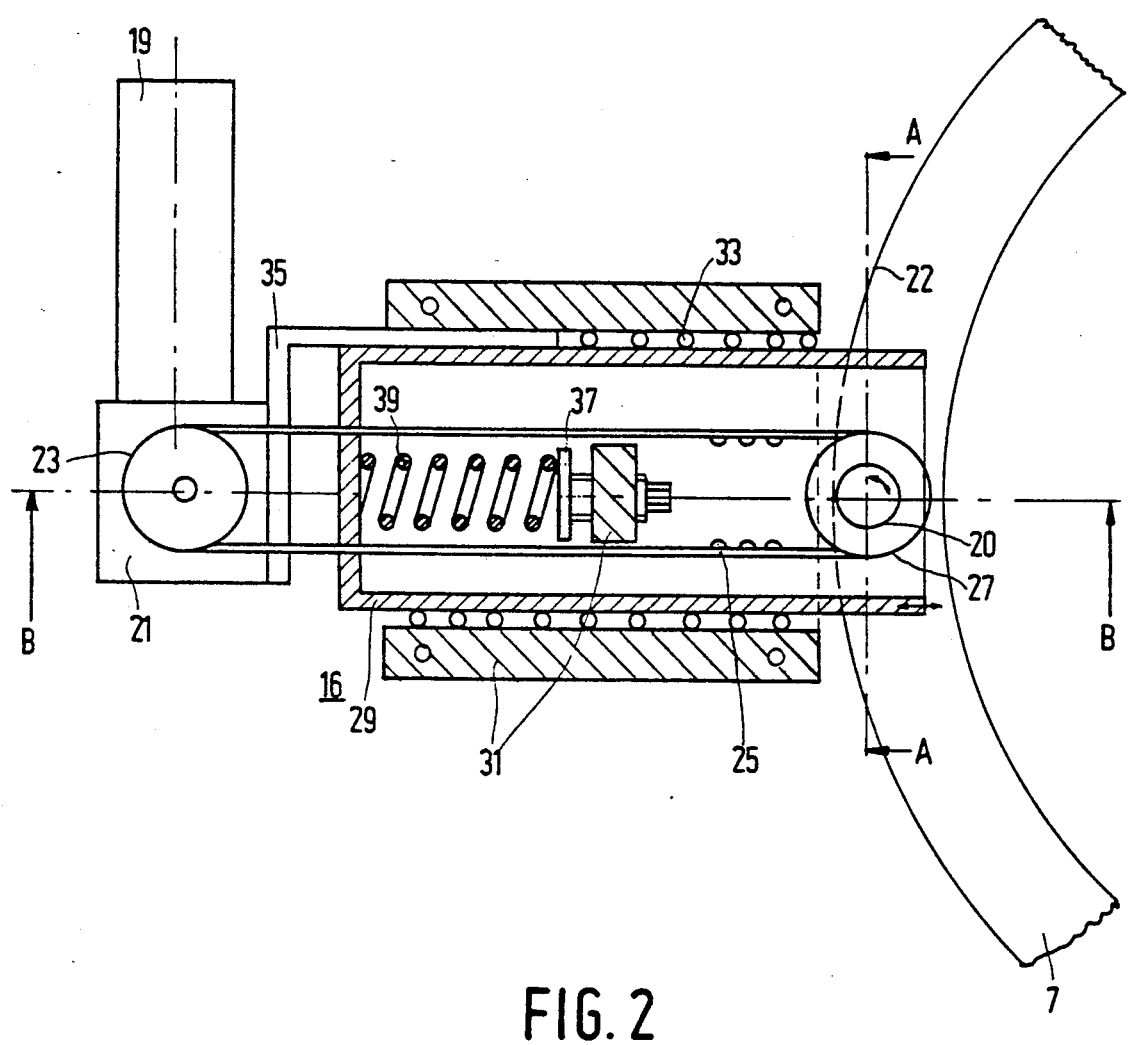
FIG. 2 is a lateral sectional view of a mount comprising displacement means in accordance with the invention which are mounted on a carriage.

FIG. 2 shows the motor 19 which is connected to a reduction gearbox 21. The gearbox 21 delivers a high torque to a gearwheel 23 at a comparatively low number of revolutions. Via a drive belt 25, for example a toothed belt, a second gearwheel 27 is driven. The gearwheel 27 is connected to the drive shaft (not shown in this Figure) which extends perpendicularly to the plane of drawing and whereto the friction roller 20 is also connected. The friction roller 20 contacts a contact face 22 of the C-shaped carrier 7. The drive shaft is journalled in a carriage 29 which is arranged in a holder 31 and which is displaceable, via a roller guide system 33, with respect to the holder 31 which forms part of the mount 3. The gearbox 21 is connected to the carriage 29 via a motor support 35. A pressure member 39 in the form of a pressure spring can be adjusted by tightening or loosening an adjusting nut 37, so that the friction roller 20 is pressed against the contact face 22 under more or less pressure. Because the motor 19 moves along with the carriage 29 when the pressure member 39 is adjusted, a tension of the toothed belt 25 remains constant.

Figure 3:
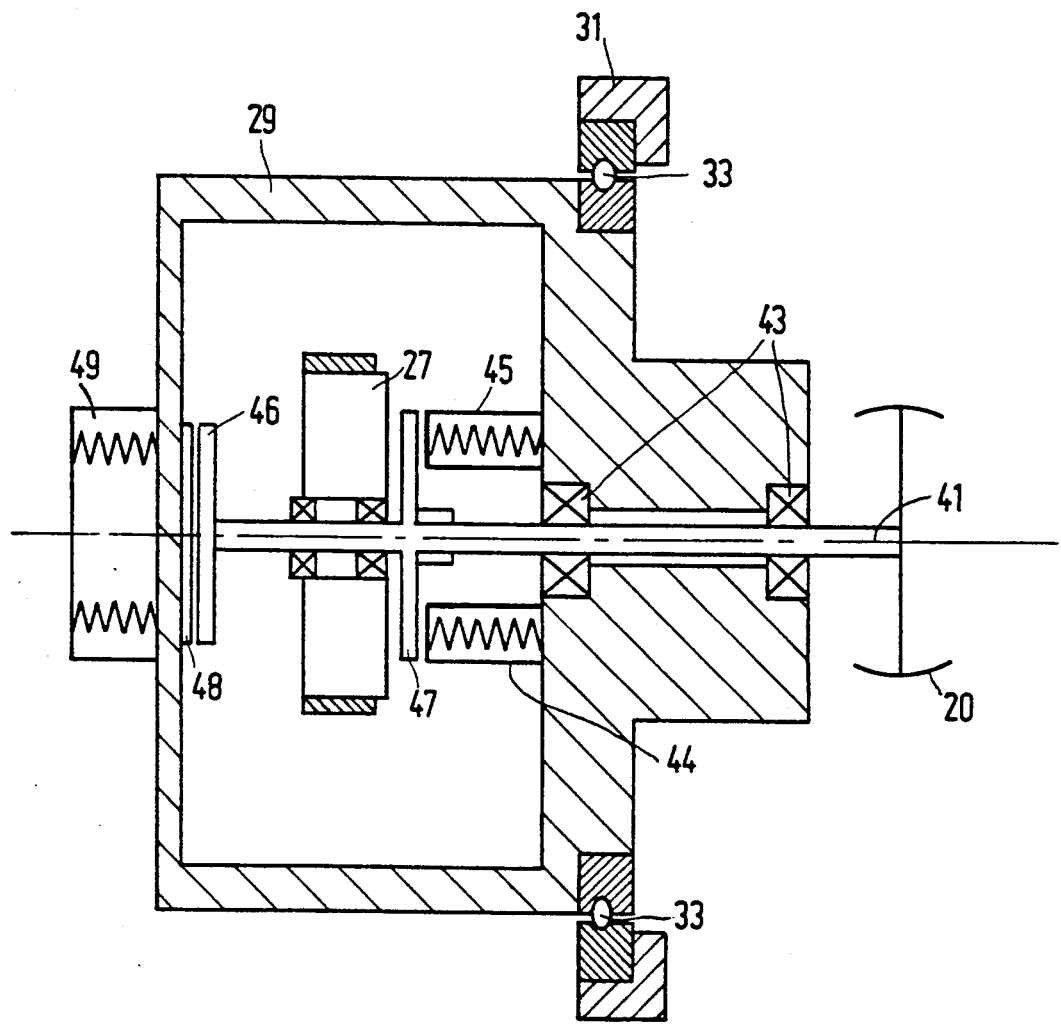
FIG. 3 is a sectional view, taken along the line A—A in FIG. 2, of a mount comprising displacement means in accordance with the invention which are mounted on a carriage.

FIG. 3 shows the friction roller 20 which is connected to the carriage 29 by way of the drive shaft 41 and ball bearings 43. In this Figure the carriage 29 is displaceable, via the roller guide system 33, in a direction extending perpendicularly to the plane of drawing with respect to the holder 31. Via an electromechanical drive coupling 44, the motor 19 can be coupled to the drive shaft 41. When a relay 45 of the drive coupling 44 is energized, the gearwheel 27 is made to mesh with a gearwheel 47 which is rigidly connected to the drive shaft 41. When the relay 45 is not energized, the gearwheel 27 can rotate freely about the shaft 41. Using a brake clutch 49, a brake disc 46 which is connected to the drive shaft 41 can be made to contact a second brake disc 48 mounted on the carriage 29. Rotation of the drive shaft 41 is thus blocked, the friction roller 20 locking the position of the carrier 7 with respect to the mount 3.

Figure 4:
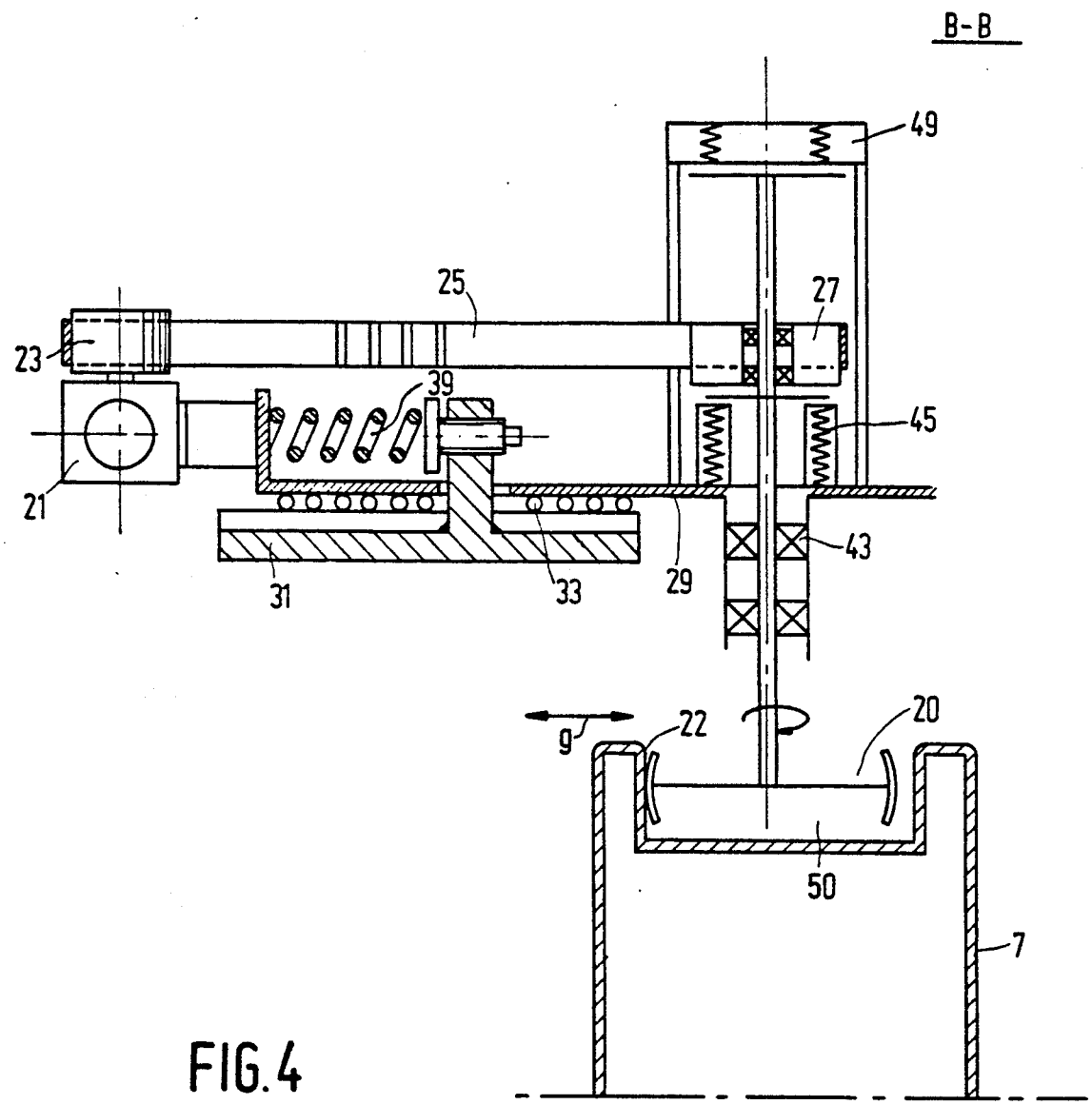
FIG. 4 is a sectional view, taken along the line B—B in FIG. 2, of a mount comprising displacement means in accordance with the invention which are mounted on a carriage.

FIG. 4 illustrates how the friction roller 20 is pressed against the contact face 22 by displacement of the carriage 29 in one of the directions denoted by an arrow g. The contact face 22 forms part of, for example a bearing groove 50 which is situated along a side face of the C-shaped carrier 7. The carrier 7 is usually made of a light material such as aluminium. The friction roller 20 is preferably made of a wear-resistant material such as stainless steel. The bearing groove 50 may also be clad with stainless steel or another metal having a comparatively high wear resistance.

What is claimed is:

1. An X-ray examination apparatus comprising:
   a column;
   a mount connected to the column and rotatable about an axis;
   a C-shaped carrier journaled in the mount and which carries an X-ray source and an X-ray detector in facing relation, said carrier being displaceable in the mount along a segment of a circle;
   carrier displacement means coupled to the mount including a drive shaft and a friction roller secured to the shaft for bearing against the carrier on a carrier contact face for displacing the carrier relative to the mount; and
   coupling means secured to the mount for selectively coupling and decoupling said friction roller to said displacement means.

2. An X-ray examination apparatus as claimed in claim 1, wherein the displacement means includes a carriage which is displaceable with respect to the mount in a direction extending transversely of the contact face, said drive shaft being journaled in said carriage and a pressure member interconnecting the carriage and the mount and pressing the friction roller against the contact face.

3. An X-ray examination apparatus as claimed in claim 2, wherein the pressure member comprises a spring.

4. An X-ray examination apparatus as claimed in claim 2 wherein the pressure member is adjustable.

5. An X-ray examination apparatus as claimed in claim 2 wherein the displacement means includes a motor selectively coupled to the drive shaft, the motor being connected to the carriage and displaceable together with the carriage with respect to the mount.

6. An X-ray examination apparatus as claimed in claim 5 wherein the motor is coupled to the drive shaft via a drive coupling.

7. An X-ray examination apparatus as claimed in claim 2 wherein the drive shaft comprises a brake member which selectively contacts, via a brake clutch, a further brake member mounted on the carriage.

8. An X-ray examination apparatus as claimed in claim 3 wherein the pressure member is adjustable.

9. An X-ray examination apparatus as claimed in claim 3 wherein the displacement means includes a motor selectively coupled to the drive shaft, the motor being connected to the carriage and displaceable together with the carriage with respect to the mount.

10. An X-ray examination apparatus as claimed in claim 4 wherein the displacement means includes a motor selectively coupled to the drive shaft, the motor being connected to the carriage and displaceable together with the carriage with respect to the mount.

11. An X-ray examination apparatus as claimed in claim 8 wherein the displacement means includes a motor selectively coupled to the drive shaft, the motor being connected to the carriage and displaceable together with the carriage with respect to the mount.

12. An X-ray examination apparatus as claimed in claim 6 wherein the drive shaft comprises a brake member which selectively contacts, via a brake clutch, a further brake member mounted on the carriage.

13. An X-ray examination apparatus as claimed in claim 8 wherein the drive shaft comprises a brake member which selectively contacts, via a brake. clutch, a further brake member mounted on the carriage.

14. The apparatus of claim 1 including locking means for selectively locking said roller in fixed bearing relation against said carrier to preclude relative displacement of the carrier to said mount.

15. The apparatus of claim 14 wherein the friction roller is substantially incompressible material for assisting in said precluding said relative displacement.

16. The apparatus of claim 1 wherein said roller is metal.

17. The apparatus of claim 14 wherein said coupling means includes first clutch means for driving said roller in the coupled state and said locking means comprises second clutch means for locking the roller in place.

18. An X-ray examination apparatus comprising:
a support;
a mount connected to the support;
a C-shaped carrier having a contact face and journaled in the mount, said carrier carrying an X-ray source and an X-ray detector in facing relation, said carrier being displaceable in the mount along a segment of a circle;
carrier displacement means coupled to the mount including a friction carrier drive roller secured for bearing against the carrier on said carrier contact face and friction roller drive means for displacing the carrier relative to the mount, said drive roller being made of relatively incompressible material; and
means for selectively locking the carrier to preclude carrier displacement relative to said mount.

19. The apparatus of claim 18 including clutch means coupled to said mount for selectively locking said drive roller.

20. The apparatus of claim 18 wherein said contact face and drive roller have metal engaging surfaces.

21. The apparatus of claim 20 wherein said surfaces are steel.

22. The apparatus of claim 18 including coupling means for selectively coupling and decoupling said roller to said displacement means.

23. The apparatus of claim 22 wherein said locking means include brake clutch means for selectively locking the roller in fixed bearing relation against said carrier to preclude said relative displacement of the carrier to said mount.

24. The apparatus of claim 18 wherein said drive means includes first clutch means for selectively coupling said drive means to said roller and second clutch means coupled to said roller for selectively locking the roller in place.

* * * * *